(12) United States Patent
Fantuzzi et al.

(10) Patent No.: US 12,721,965 B2
(45) **Date of Patent: *Sep. 1, 2026**

(54) OVERMOLD TECHNIQUE FOR PEEL-AWAY INTRODUCER DESIGN

(71) Applicants: ABIOMED, Inc., Danvers, MA (US); Oscor, Inc., Palm Harbor, FL (US)

(72) Inventors: Glen Fantuzzi, Danvers, MA (US); Michael Tafone, Danvers, MA (US); Jeffrey Drum, Palm Harbor, FL (US)

(73) Assignees: ABIOMED, Inc., Danvers, MA (US); Oscor, Inc., Palm Harbor, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/788,325

(22) Filed: Jul. 30, 2024

(65) Prior Publication Data

US 2025/0065075 A1 Feb. 27, 2025

Related U.S. Application Data

(63) Continuation of application No. 18/211,610, filed on Jun. 20, 2023, now Pat. No. 12,076,497, which is a (Continued)

(51) Int. Cl.
*A61M 25/00* (2006.01)
*A61M 25/06* (2006.01)

(Continued)

(52) U.S. Cl.
CPC .... *A61M 25/0009* (2013.01); *A61M 25/0014* (2013.01); *A61M 25/0668* (2013.01);

(Continued)

(58) Field of Classification Search
None
See application file for complete search history.

(56) References Cited

U.S. PATENT DOCUMENTS 4,317,445 A 3/1982 Robinson
4,380,252 A 4/1983 Gray et al.

(Continued)

FOREIGN PATENT DOCUMENTS

CN 104623790 A 5/2015
EP 77827 A1 5/1983

(Continued)

OTHER PUBLICATIONS

Decision to Grant received in corresponding Japanese Application No. 2019-551498 dated Sep. 1, 2021, 6 pp.

(Continued)

*Primary Examiner* — Abbas Rashid
*Assistant Examiner* — Adrianna N Konves
(74) *Attorney, Agent, or Firm* — Botos Churchill IP Law LLP

(57) ABSTRACT

A method for manufacturing a medical introducer includes placing an introducer sheath onto a mandrel, and overmolding an introducer hub onto a proximal end of the introducer sheath. The introducer sheath has one or more score lines formed on an inner surface and the mandrel has a number of surface protrusions so that when the introducer sheath is positioned on the mandrel, each of the surface protrusions contacts one of the score lines formed on the introducer sheath. The surface protrusions on the mandrel prevent plastic material from the introducer hub from contacting the score lines thereby maintaining the score lines during the overmolding.

11 Claims, 5 Drawing Sheets

Related U.S. Application Data continuation of application No. 17/741,627, filed on May 11, 2022, now Pat. No. 11,717,640, which is a continuation of application No. 15/834,783, filed on Dec. 7, 2017, now Pat. No. 11,364,363.

(60) Provisional application No. 62/431,671, filed on Dec. 8, 2016.

(51) Int. Cl.
*B29C 45/14* (2006.01)
*B29L 31/00* (2006.01)

(52) U.S. Cl.
CPC .. *B29C 45/14065* (2013.01); *B29C 45/14336* (2013.01); *A61M 25/0097* (2013.01); *B29L 2031/7542* (2013.01)

(56) References Cited

U.S. PATENT DOCUMENTS 4,402,685 A 9/1983 Buehler et al.
4,569,347 A 2/1986 Frisbie
4,651,751 A 3/1987 Swendson et al.
4,699,611 A 10/1987 Bowden
4,798,594 A 1/1989 Hillstead
4,895,565 A 1/1990 Hillstead
5,069,674 A 12/1991 Fearnot et al.
5,139,486 A 8/1992 Moss
5,180,372 A 1/1993 Vegoe et al.
5,221,255 A 6/1993 Mahurkar et al.
5,234,425 A 8/1993 Fogarty et al.
5,250,033 A 10/1993 Evans et al.
5,279,596 A 1/1994 Castaneda et al.
5,304,142 A 4/1994 Liebl et al.
5,312,355 A 5/1994 Lee
5,320,611 A 6/1994 Bonutti et al.
5,380,304 A 1/1995 Parker
5,395,341 A 3/1995 Slater
5,397,310 A 3/1995 Chu et al.
5,397,311 A 3/1995 Walker et al.
5,405,338 A 4/1995 Kranys
5,407,430 A 4/1995 Peters
5,409,463 A 4/1995 Thomas et al.
5,409,469 A 4/1995 Schaerf
5,488,960 A 2/1996 Toner
5,492,530 A 2/1996 Fischell et al.
5,536,255 A 7/1996 Moss
5,573,517 A 11/1996 Bonutti et al.
5,599,326 A 2/1997 Carter
5,653,697 A 8/1997 Quiachon et al.
5,713,867 A 2/1998 Morris
5,752,937 A 5/1998 Otten et al.
5,795,341 A 8/1998 Samson
5,827,242 A 10/1998 Follmer et al.
5,911,702 A 6/1999 Romley et al.
5,935,122 A 8/1999 Fourkas et al.
5,951,518 A 9/1999 Licata et al.
5,971,993 A 10/1999 Hussein et al.
6,042,578 A 3/2000 Dinh et al.
6,068,622 A 5/2000 Sater et al.
6,080,141 A 6/2000 Castro et al.
6,165,163 A 12/2000 Chien et al.
6,197,014 B1 3/2001 Samson et al.
6,197,016 B1 3/2001 Fourkas et al.
6,217,565 B1 4/2001 Cohen
6,258,080 B1 7/2001 Samson
6,290,692 B1 9/2001 Klima et al.
6,319,244 B2 11/2001 Suresh et al.
6,338,730 B1 1/2002 Bonutti et al.
6,363,273 B1 3/2002 Mastrorio et al.
6,379,346 B1 4/2002 McIvor et al.
6,423,052 B1 7/2002 Escano
6,428,556 B1 8/2002 Chin
6,454,744 B1 9/2002 Spohn et al.
6,508,966 B1 1/2003 Castro et al.
6,544,270 B1 4/2003 Zhang
6,562,049 B1 5/2003 Norlander et al.
6,589,227 B2 7/2003 Soenderskov
6,613,038 B2 9/2003 Bonutti et al.
6,652,508 B2 11/2003 Griffin et al.
6,692,462 B2 2/2004 Mackenzie et al.
6,702,972 B1 3/2004 Markle
6,740,073 B1 5/2004 Saville
6,749,600 B1 6/2004 Levy
6,814,715 B2 11/2004 Bonutti et al.
6,824,553 B1 11/2004 Samson et al.
6,827,710 B1 12/2004 Mooney et al.
6,852,261 B2 2/2005 Benjamin
6,866,660 B2 3/2005 Garabedian et al.
6,881,211 B2 4/2005 Schweikert et al.
6,887,417 B1 5/2005 Gawreluk et al.
6,939,327 B2 9/2005 Hall et al.
6,939,337 B2 9/2005 Parker et al.
7,018,372 B2 3/2006 Casey et al.
7,025,746 B2 4/2006 Tal
7,037,295 B2 5/2006 Tiernan et al.
7,101,353 B2 9/2006 Lui et al.
7,144,411 B2 12/2006 Ginn et al.
7,169,118 B2 1/2007 Reynolds et al.
7,226,433 B2 6/2007 Bonnette et al.
7,357,794 B2 4/2008 Makower et al.
7,367,967 B2 5/2008 Eidenschink
7,422,571 B2 9/2008 Schweikert et al.
7,438,712 B2 10/2008 Chouinard
7,497,844 B2 3/2009 Spear et al.
7,524,305 B2 4/2009 Moyer
7,540,865 B2 6/2009 Griffin et al.
7,628,769 B2 12/2009 Grandt et al.
7,637,903 B2 12/2009 Lentz et al.
7,645,273 B2 1/2010 Lualdi
7,704,245 B2 4/2010 Dittman et al.
7,713,260 B2 5/2010 Lessard et al.
7,722,567 B2 5/2010 Tal
7,731,694 B2 6/2010 Becker et al.
7,744,571 B2 6/2010 Fisher et al.
7,749,185 B2 7/2010 Wilson et al.
7,766,820 B2 8/2010 Core
7,833,218 B2 11/2010 Lunn et al.
7,837,671 B2 11/2010 Eversull et al.
7,871,398 B2 1/2011 Chesnin et al.
7,905,877 B1 3/2011 Jimenez et al.
7,909,798 B2 3/2011 Osypka
7,963,948 B2 6/2011 Melsheimer
7,968,038 B2 6/2011 Dittman et al.
7,985,213 B2 7/2011 Parker
7,989,042 B2 8/2011 Obara et al.
7,993,305 B2 8/2011 Ye et al.
8,021,409 B2 9/2011 Aggerholm
8,070,898 B2 12/2011 Eversull et al.
8,123,726 B2 2/2012 Searfoss et al.
8,147,452 B2 4/2012 Nardeo et al.
8,206,375 B2 6/2012 Snow
8,231,551 B2 7/2012 Griffin et al.
8,246,574 B2 8/2012 Jacobs et al.
8,257,298 B2 9/2012 Hamboly
8,273,059 B2 9/2012 Nardeo et al.
8,292,827 B2 10/2012 Musbach et al.
8,298,189 B2 10/2012 Fisher et al.
8,303,570 B2 11/2012 Gregorich et al.
8,317,754 B2 11/2012 Leeflang et al.
8,343,136 B2 1/2013 Howat et al.
8,366,720 B2 2/2013 Mitelberg et al.
8,377,035 B2 2/2013 Zhou et al.
8,398,696 B2 3/2013 Buiser et al.
8,475,431 B2 7/2013 Howat
8,529,719 B2 9/2013 Pingleton et al.
8,591,495 B2 11/2013 Fischell et al.
8,597,277 B2 12/2013 Lenker et al.
8,636,270 B2 1/2014 Ostrovsky
8,672,888 B2 3/2014 Tal
8,684,963 B2 4/2014 Qiu et al.
8,728,055 B2 5/2014 Stehr et al.
8,758,402 B2 6/2014 Jenson et al.

(56) References Cited

U.S. PATENT DOCUMENTS

| | | | |
|---|---|---|---|
| 8,821,510 | B2 | 9/2014 | Parker |
| 8,974,420 | B2 | 3/2015 | Searfoss et al. |
| 9,095,684 | B2 | 8/2015 | Martinez-Arraras |
| 9,168,359 | B2 | 10/2015 | Rowe et al. |
| 9,295,809 | B2 | 3/2016 | Sheetz |
| 9,320,873 | B2 | 4/2016 | Okamura |
| 9,352,116 | B2 | 5/2016 | Guo et al. |
| 9,427,551 | B2 | 8/2016 | Leeflang et al. |
| 9,492,636 | B2 | 11/2016 | Heideman et al. |
| 9,517,323 | B2 | 12/2016 | Kimmel et al. |
| 9,539,368 | B2 | 1/2017 | Haslinger et al. |
| 9,539,411 | B2 | 1/2017 | Cully et al. |
| 9,545,496 | B2 | 1/2017 | Hiroshige et al. |
| 9,597,481 | B2 | 3/2017 | Ishikawa |
| 9,616,195 | B2 | 4/2017 | Lippert et al. |
| 9,622,892 | B2 | 4/2017 | Baker et al. |
| 9,629,978 | B2 | 4/2017 | Eversull et al. |
| 9,707,373 | B2 | 7/2017 | Nielsen |
| 9,884,169 | B2 | 2/2018 | Bierman et al. |
| 9,901,706 | B2 | 2/2018 | Storbeck et al. |
| 9,937,319 | B1 | 4/2018 | Leeflang et al. |
| 9,980,710 | B2 | 5/2018 | Seifert et al. |
| 9,981,115 | B2 | 5/2018 | Merk et al. |
| 9,987,460 | B2 | 6/2018 | Brustad et al. |
| 10,065,015 | B2 | 9/2018 | Leeflang et al. |
| 10,076,639 | B2 | 9/2018 | Guo et al. |
| 10,086,172 | B2 | 10/2018 | Okamura |
| 10,124,151 | B2 | 11/2018 | Okamura et al. |
| 2002/0058910 | A1 | 5/2002 | Hermann et al. |
| 2002/0072712 | A1 | 6/2002 | Nool et al. |
| 2003/0083623 | A1 | 5/2003 | Berg et al. |
| 2004/0059296 | A1 | 3/2004 | Godfrey |
| 2004/0122360 | A1 | 6/2004 | Waldhauser et al. |
| 2004/0267202 | A1 | 12/2004 | Potter |
| 2004/0267203 | A1 | 12/2004 | Potter et al. |
| 2005/0090802 | A1 | 4/2005 | Connors et al. |
| 2005/0149105 | A1 | 7/2005 | Leeflang et al. |
| 2005/0182387 | A1 | 8/2005 | Webler |
| 2006/0052749 | A1 | 3/2006 | Moyer |
| 2006/0095050 | A1 | 5/2006 | Hartley et al. |
| 2006/0111614 | A1 | 5/2006 | Saadat et al. |
| 2006/0135981 | A1 | 6/2006 | Lenker et al. |
| 2006/0161135 | A1 | 7/2006 | Vanderwoude |
| 2006/0200110 | A1 | 9/2006 | Lentz et al. |
| 2006/0287574 | A1 | 12/2006 | Chin |
| 2008/0046005 | A1 | 2/2008 | Lenker et al. |
| 2008/0051734 | A1 | 2/2008 | Bonutti et al. |
| 2008/0051821 | A1 | 2/2008 | Gephart |
| 2008/0082165 | A1 | 4/2008 | Wilson et al. |
| 2008/0306442 | A1 | 12/2008 | Bardsley et al. |
| 2009/0043285 | A1 | 2/2009 | Stehr et al. |
| 2009/0192463 | A1 | 7/2009 | Nardeo et al. |
| 2009/0240202 | A1 | 9/2009 | Drasler et al. |
| 2010/0082000 | A1 | 4/2010 | Honeck et al. |
| 2010/0228178 | A1 | 9/2010 | Mcgraw |
| 2010/0268196 | A1 | 10/2010 | Hastings et al. |
| 2010/0305509 | A1 | 12/2010 | Osypka et al. |
| 2012/0245527 | A1 | 9/2012 | Stephens et al. |
| 2013/0018309 | A1 | 1/2013 | Ewing et al. |
| 2013/0131718 | A1 | 5/2013 | Jenson et al. |
| 2013/0317438 | A1 | 11/2013 | Ellingwood et al. |
| 2013/0317481 | A1 | 11/2013 | Ellingwood et al. |
| 2014/0031843 | A1 | 1/2014 | Rottenberg et al. |
| 2015/0051541 | A1 | 2/2015 | Kanemasa et al. |
| 2015/0174364 | A1 | 6/2015 | Kennelly et al. |
| 2015/0201963 | A1 | 7/2015 | Snow |
| 2015/0352330 | A1 | 12/2015 | Wasdyke et al. |
| 2016/0001042 | A1 | 1/2016 | Worley et al. |
| 2016/0051798 | A1 | 2/2016 | Weber et al. |
| 2016/0058976 | A1 | 3/2016 | Okamura et al. |
| 2016/0066948 | A1 | 3/2016 | Ellingwood et al. |
| 2016/0096000 | A1 | 4/2016 | Mustapha |
| 2016/0220358 | A1 | 8/2016 | Wilson et al. |
| 2016/0346507 | A1 | 12/2016 | Jackson et al. |
| 2016/0346508 | A1 | 12/2016 | Williams et al. |
| 2016/0354583 | A1 | 12/2016 | Ellingwood et al. |
| 2016/0375222 | A1 | 12/2016 | Wada |
| 2017/0043135 | A1 | 2/2017 | Knutsson |
| 2017/0056063 | A1 | 3/2017 | Ellingwood et al. |
| 2017/0072165 | A1 | 3/2017 | Lim et al. |
| 2017/0087331 | A1 | 3/2017 | Cully et al. |
| 2017/0113018 | A1 | 4/2017 | Shimizu et al. |
| 2017/0120008 | A1 | 5/2017 | Burkholz et al. |
| 2017/0238965 | A1 | 8/2017 | Murphy |
| 2017/0252535 | A1 | 9/2017 | Ganske et al. |
| 2017/0274179 | A1 | 9/2017 | Sullivan et al. |
| 2017/0281908 | A1 | 10/2017 | Ellingwood et al. |
| 2017/0296777 | A1 | 10/2017 | Heisel et al. |
| 2017/0333682 | A1 | 11/2017 | Nardeo |
| 2017/0340860 | A1 | 11/2017 | Eberhardt et al. |
| 2018/0001061 | A1 | 1/2018 | Okamura et al. |
| 2018/0015254 | A1 | 1/2018 | Cragg et al. |
| 2018/0043138 | A1 | 2/2018 | Chu |
| 2018/0056037 | A1 | 3/2018 | Shimizu |
| 2018/0228502 | A1 | 8/2018 | Shaffer et al. |
| 2018/0250498 | A1 | 9/2018 | Stern et al. |
| 2018/0256847 | A1 | 9/2018 | Lareau et al. |
| 2018/0344987 | A1 | 12/2018 | Lancette et al. |
| 2018/0361116 | A1 | 12/2018 | Quick et al. |

FOREIGN PATENT DOCUMENTS

| | | | |
|---|---|---|---|
| EP | 1053039 | A1 | 11/2000 |
| EP | 1212185 | A1 | 6/2002 |
| EP | 1444000 | A2 | 8/2004 |
| EP | 1631343 | A1 | 3/2006 |
| EP | 1656963 | A1 | 5/2006 |
| EP | 1853331 | A2 | 11/2007 |
| EP | 2068994 | A2 | 6/2009 |
| EP | 2335764 | A1 | 6/2011 |
| EP | 2429628 | A2 | 3/2012 |
| EP | 2473123 | A1 | 7/2012 |
| EP | 2703069 | A2 | 3/2014 |
| EP | 3132823 | A1 | 2/2017 |
| EP | 3311873 | A1 | 4/2018 |
| EP | 3347079 | A1 | 7/2018 |
| EP | 3395301 | A1 | 10/2018 |
| GB | 252863 | A | 6/1926 |
| JP | 19968257128 | | 10/1996 |
| JP | 2004357847 | A | 12/2004 |
| JP | 2008543440 | A | 12/2008 |
| JP | 4695878 | B2 | 6/2011 |
| JP | 5581139 | B2 | 8/2014 |
| JP | 04326702 | | 9/2020 |
| WO | 93008986 | A1 | 5/1993 |
| WO | 93015872 | A1 | 8/1993 |
| WO | 97037713 | A1 | 10/1997 |
| WO | 2000048659 | A2 | 8/2000 |
| WO | 2001041858 | A2 | 6/2001 |
| WO | 2006138356 | A2 | 12/2006 |
| WO | 2009114556 | A2 | 9/2009 |
| WO | 2017094697 | A1 | 6/2017 |
| WO | 2018191547 | A1 | 10/2018 |

OTHER PUBLICATIONS

International Search Report and Written Opinion in International Application No. PCT/US2017/065046 dated Mar. 22, 2018 (5 pages).

Office Action received in corresponding Indian Application No. 201917026180 dated Sep. 15, 2021, 7 pp.

Written Opinion for corresponding Singapore Application No. 11201905183X dated Sep. 7, 2020 (4 pages).

Office Action from corresponding Israel Patent Application No. 313991 dated Mar. 20, 2025 (4 pp.).

Office Action from corresponding Japanese Patent Application No. 2023-186154 dated Mar. 17, 2025 (8 pp.).

OVERMOLD TECHNIQUE FOR PEEL-AWAY INTRODUCER DESIGN

CROSS-REFERENCE TO RELATED APPLICATIONS

The present application is a continuation of U.S. patent application Ser. No. 18/211,610, filed Jun. 20, 2023, now U.S. Pat. No. 12,076,497, which is a continuation of U.S. patent application Ser. No. 17/741,627, filed May 11, 2022, now U.S. Patent No, 11,717,640, which is a continuation of U.S. patent application Ser. No. 15/834,783, filed Dec. 7, 2017, now U.S. Pat. No. 11,364,363, which claims the benefit of the filing date of U.S. Provisional Patent Application No. 62/431,671, filed on Dec. 8, 2016, the entire disclosures of which are hereby incorporated herein by reference.

BACKGROUND OF THE INVENTION

Peel-away introducers are disposable medical devices used in a cardiac catheterization or other medical setting to deliver medical devices into the vasculature. Standard peel-away introducers include a proximal plastic hub coupled to a sheath. Medical devices can be inserted through the plastic hub and into the sheath, through which the device can be placed in a patient's body. Intravascular medical devices, such as intracardiac blood pumps, catheters, guidewires, or leads, can be introduced into a patient's vasculature through a peel-away introducer. Once the medical device has been positioned, the peel-away introducer can be removed. In one approach, the operator breaks the introducer by cracking the plastic introducer hub and peeling down the shaft of the sheath body. In order to break the peel-away introducer, the operator grasps the molded hub and breaks it at the proximal end of the sheath along axial notches or scorings. The sheath tears along perforations or scorings down one or both sides of the sheath and can be peeled axially. The peel-away introducer allows the introducer to be removed after a medical device is inserted into a patient through the introducer without disturbing or removing the medical device.

In a common manufacturing technique, peel-away introducers are formed from an extruded plastic tube with axial notches in a hub body. A hub body including notches and/or wings to facilitate breaking is overmolded onto an extruded plastic sheath or tube. The plastic tube is first assembled over a corepin or mandrel which defines and maintains the inner cavity of the hub and inner diameter and geometry of the sheath. The mandrel and extruded sheath are then placed into a mold cavity allowing for molten plastic to be injected and cooled, creating the plastic hub that the user breaks to initiate peeling.

In the overmolding technique, after the mandrel and extruded sheath are placed into a mold, molten plastic in injected into the mold. The plastic cools around the sheath in the shape of the mold, forming the hub body. The injected plastic is maintained at a high temperature when it is introduced to the mold, and the heat from the injected plastic surrounding the sheath may be sufficient to heat a top layer of the sheath plastic such that the plastic of the sheath may start to flow in a process called reflowing. The portion of the sheath disposed inside the hub of the assembly may lose its internal scoring or notching during the molding process if the heat of the injected plastic reflows into one or more of the scores/notches. As a result, the forces required to break the hub may be excessive or inconsistent because the sheath does not include a weakened section of one of the scores/ notches. Furthermore, when the plastic of the sheath is reflowed and the scoring is removed in the section of the sheath within the hub, there is an increased risk that during the breaking of the hub the tear will not propagate to the scoring in the sheath body outside the section in the overmolded hub leading to a defective peel-away introducer sheath.

SUMMARY OF THE INVENTION

Described herein are methods and systems for producing a peel-away introducer including an overmolded hub while maintaining the scoring of the sheath. During overmolding, a mandrel designed with outer surface protrusions on which the sheath is assembled, maintains the inner scorings of the sheath through the injection molding process despite the application of extreme heat. With the internal scorings of the sheath maintained, when the hub is broken by an operator, the proximal section of the sheath tube in the overmolded hub breaks more easily and with less required force. Sheaths manufactured by the methods disclosed herein can also peel more easily.

In one aspect, a method for manufacturing a medical introducer includes placing an introducer sheath onto a mandrel, and overmolding an introducer hub onto a proximal end of the introducer sheath. The introducer sheath has one or more score lines formed on an inner surface. The mandrel has a number of surface protrusions so that when the introducer sheath is positioned on the mandrel, each of the surface protrusions contacts one of the score lines formed on the introducer sheath and prevents plastic material from the introducer hub from contacting the score lines.

In some implementations, the number of surface protrusions on the mandrel is equal to the number of score lines formed on the sheath. In some implementations, the introducer hub includes a number of notches. In some implementations, the number of notches in the introducer hub is equal to the number of score lines formed on the sheath and also equal to the number of surface protrusions on the mandrel. In some implementations, at least one of the number of notches is aligned with a score line formed on the sheath. In some implementations, at least two notches are aligned with a score line formed on the sheath. In some implementations, the introducer hub and introducer sheath are configured to be broken into at least two pieces along the notches and score lines.

In some implementations, the number of surface protrusions on the mandrel is not equal to the number of score lines formed on the sheath. In some implementations, at least one of the number of score lines formed on the inner surface of the introducer sheath is removed during the overmolding. In some implementations, the number of surface protrusions on the mandrel is equal to a desired number of score lines in the sheath.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION OF THE DRAWINGS

Following below are more detailed descriptions of various concepts related to inventive methods of manufacturing a peel-away medical introducer. It should be appreciated that various concepts introduced above and discussed in greater detail below may be implemented in any number of ways, as the disclosed concepts are not limited to any particular manner of implementation. For example, though peel-away introducer sheaths are depicted herein having two axial notches which divide the introducer hub and underlying sheath into two sections, the introducer hub and sheath may be manufactured to have any number of axial notches or perforations so as to allow parting into any number of portions along an axial direction. Furthermore, although surface protrusions of a mandrel are described with reference to maintaining score lines on a sheath for use in a peel-away introducer, the surface protrusions on the mandrel may be used to protect other features of the internal geometry of a sheath during any overmolding or heat-treating process. Examples of implementations and applications are provided primarily for illustrative purposes.

The methods and systems described herein enable production of a peel-away introducer including an overmolded hub while maintaining the scoring of the sheath. The mandrel for holding the hub and the sheath can have one or more outer elongate protrusions formed along an outer surface thereof. A protrusion can contact each of the corresponding inner scorings of the sheath so that when heat is applied the score lines are maintained through the injection molding process rather than filled with material from the hub or the sheath (e.g., plastic that has melted during heat application). With the internal scorings of the sheath maintained, when the hub is broken by an operator, the proximal section of the sheath tube in the overmolded hub breaks more easily and with less required force than if this material had flowed into the score lines and hardened. Additionally, with the score lines in the introducer sheath maintained, the hub can be broken and the sheath peeled longitudinally to facilitate removal of the introducer hub assembly. The overmolding method described herein promotes appropriate breaking of the introducer hub and peeling of the sheath as designed.

Figure 1A:
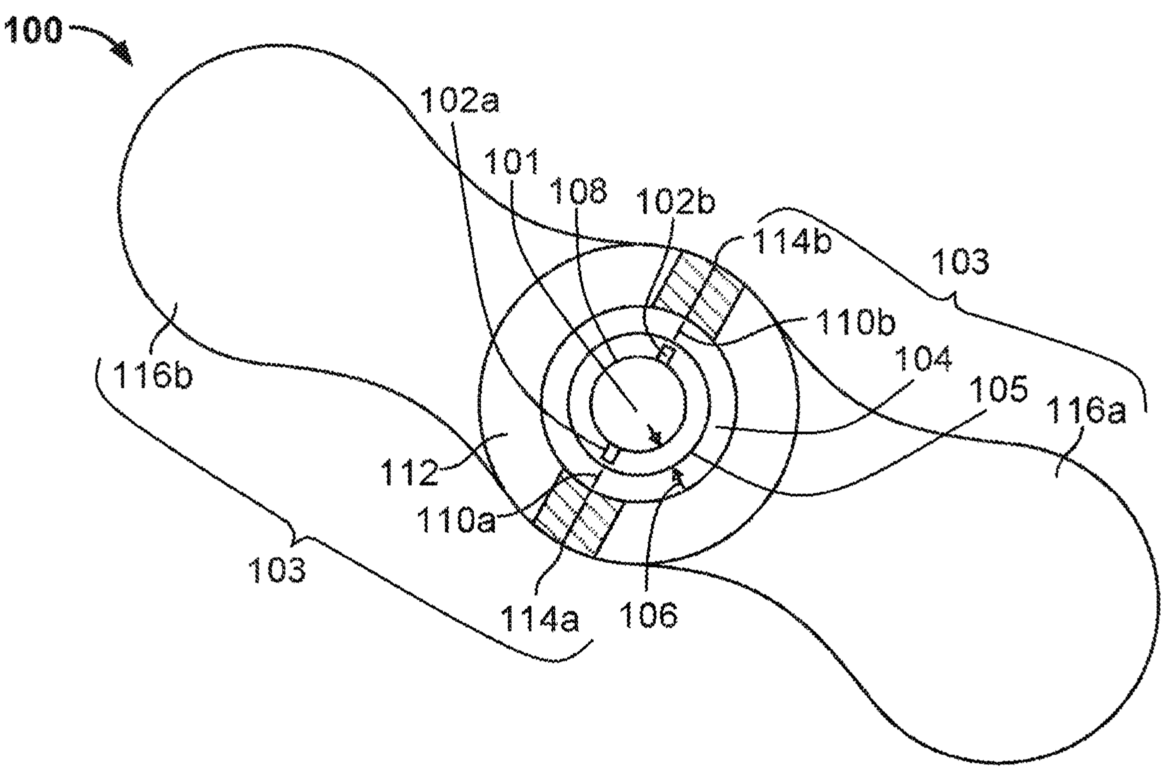
FIG. 1A shows a top view of an introducer hub molded over a sheath during the manufacture process according to an embodiment.

FIG. 1A shows a top view of an introducer hub and mandrel assembly 100 including a hub body 112 molded over an introducer sheath 104 during the manufacture process. The introducer hub assembly 103 includes an introducer sheath 104, a first score line 110*a*, a second score line 110*b*, a hub body 112, a first notch 114*a*, a second notch 114*b*, a first wing 116*a*, and a second wing 116*b*. The first score line 110*a* and the second score line 110*b* are on opposite sides of the introducer sheath 104. The introducer sheath 104 is positioned over a mandrel 101 (also called a corepin) having a first surface protrusion 102*a* and a second surface protrusion 102*b* on opposite sides of the mandrel 101. The first surface protrusion 102*a* and the second surface protrusion 102*b* are configured to coincide with the first score line 110*a* and the second score line 110*b* in the introducer sheath 104. After the introducer sheath 104 is positioned over the mandrel 101 with the first surface protrusion 102*a* and the second surface protrusion 102*b* aligned with the first score line 110*a* and the second score line 110*b* in the introducer sheath 104, the introducer hub body 112 can be overmolded over the proximal end of the introducer sheath 104. The first notch 114*a* and the second notch 114*b* are aligned with the first score line 110*a* and the second score line 110*b* in the introducer sheath 104 to facilitate breaking of the introducer hub assembly 103.

The mandrel 101 with the first surface protrusion 102*a* and the second surface protrusion 102*b* is shaped to maintain the inner geometry of the introducer sheath 104. The introducer sheath 104 fits tightly over the mandrel 101 in preparation for overmolding of the introducer hub assembly 103. There may be some distance 106 between an outer surface 108 of the mandrel 101 and an inner surface 105 of the introducer sheath 104, but in most cases the distance 106 is minimized such that the outer surface 108 of the mandrel 101 is in contact with the inner surface 105 of the introducer sheath 104 in areas which are to be protected during overmolding, such as at the first score line 110*a* and the second score line 110*b*. In some implementations, the distance 106 between the outer surface 108 of the mandrel 101 and the inner surface 105 of the introducer sheath 104 in areas which are not protected during overmolding is e.g., 0 mm, 0.1 mm, 0.2 mm, 0.3 mm, or 0.4 mm or it can be structured at any other suitable distance. The surface protrusions 102*a* and 102*b* may be set at a desired height from the body of the mandrel 101. In some implementations, the surface protrusions 102*a* and 102*b* extend from the surface of the mandrel 101 by about 0.05 mm, 0.1 mm, 0.2 mm, 0.3 mm, or any suitable height. In certain embodiments, the distance between the outer surface 108 of the mandrel 101 and an inner surface 105 of the introducer sheath 104 is between about 0 mm and 0.4 mm, while the protrusions extend from the outer surface 108 of the mandrel 101 and have a height of about 0.05 mm to 0.3 mm. In some implementations, the surface protrusions have a shape which is square, rectangular, cylindrical, or any other suitable shape. In some implementations, the protrusions extend longitudinally along the mandrel. In some implementations, the protrusions extend in a helix along the mandrel.

With the introducer sheath 104 fit over the mandrel 101, the introducer hub assembly 103 can be formed onto the sheath 104 such as by being injection molded over the introducer sheath 104. The injection molding process exposes the proximal end of the introducer sheath 104 to high temperatures and/or pressures which can cause reflow of the plastic from which the introducer sheath 104 is formed. Reflowing plastic may cover or completely fill the first score line 110*a* and the second score line 110*b* in the introducer sheath 104 if the first score line 110*a* and the second score line 110*b* are not protected by a corresponding protrusion. The first surface protrusion 102*a* and the second surface protrusion 102*b* extend into the first score line 110*a* and the second score line 110*b* such that even if the introducer sheath 104 is heated and reflow occurs, the first score line 110*a* and the second score line 110*b* are maintained.

If the first score line 110*a* and the second score line 110*b* are altered or removed by reflow of the plastic during construction, the introducer sheath 104 may not separate properly during breaking of the introducer hub assembly 103 after use. The hub body 112 may break as designed at first notch 114*a* and second notch 114*b* when an outward or downward force is applied to the first wing 116*a* and second wing 116*b*. However, if the first score line 110*a* and the second score line 110*b* have been damaged, the separation may not propagate to the introducer sheath 104, or from a proximal portion of the introducer sheath 104 to a more distal portion not in contact with the introducer hub assembly 103. As a result, it may be difficult or uncomfortable for an operator to apply the additional or excessive force required in order to initiate the breaking of the introducer hub assembly 103.

Though the introducer sheath 104 is depicted here having two score lines, the first score line 110*a* and the second score line 110*b*, the introducer sheath 104 may be configured with any number of score lines. In some implementations, the introducer sheath is configured with one score line, two score lines, three score lines, four score lines, six score lines, ten score lines, or any other suitable number of score lines. The score lines may be formed as perforations, scorings, indentations or by any other suitable means.

The mandrel 101 is depicted here having two surface protrusions, the first surface protrusion 102*a* and the second surface protrusion 102*b*, but may have any suitable number of surface protrusions. In some implementations, the mandrel 101 has one surface protrusion, two surface protrusions, three surface protrusions, four surface protrusions, six surface protrusions, or any other suitable number of surface protrusions. The mandrel 101 may have a number of surface protrusions equal to the number of score lines on the introducer sheath 104. Alternatively, the mandrel 101 may have a number of surface protrusions which is less than the number of score lines on the introducer sheath 104. If the number of surface protrusions is less than the number of score lines on the introducer sheath 104, any additional score lines on the introducer sheath 104 may be removed by reflow of material during the manufacture of the introducer hub assembly 103 overlay. For example, if an introducer sheath 104 has three score lines, but only two are desired for an introducer hub assembly a mandrel with only two surface protrusions may be used to protect two of the three score lines on the introducer sheath during overmolding. Alternatively, the mandrel 101 may have a number of surface protrusions that is greater than the number of score lines on the introducer sheath 104 such that only some of the total surface protrusions contact the score lines. This can allow, for example, the mandrel 101 to be configured to assemble sheaths having varying number of score lines.

Figure 1B:
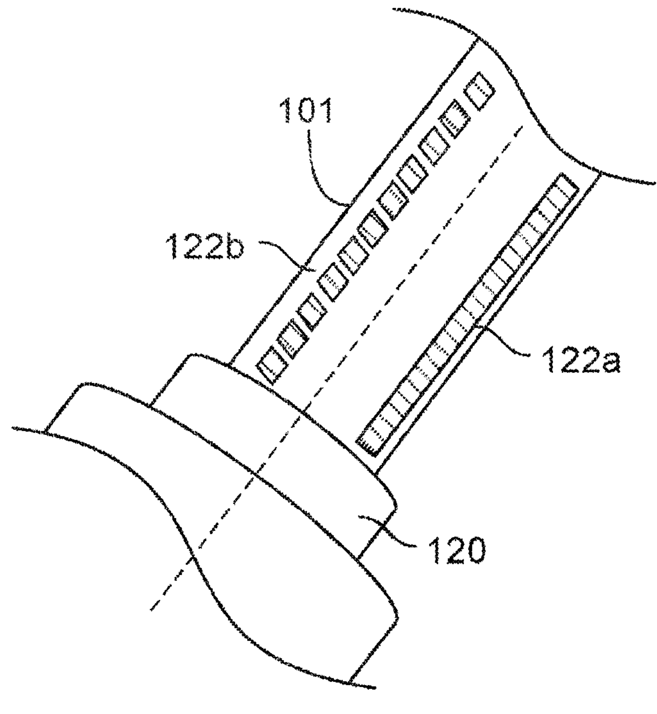
FIG. 1B shows a perspective view of a mandrel having both continuous surface protrusions and surface protrusions configured as a series of protrusions.

The surface protrusions on the mandrel 101 may be matched to the type of score lines on the introducer sheath 104, as shown in FIG. 1B. FIG. 1B includes a mandrel 101 extending from a base 120 with a first surface protrusion 122*a* and a second surface protrusion 122*b*. The first surface protrusion 122*a* is configured as a continuous protrusion from the outer surface of the mandrel 101 which would contact a score line of an introducer sheath along an entire length without interruption. The second surface protrusion 122*b* is configured as a series of surface protrusions arranged in a line along the mandrel 101. The second surface protrusion 122*b* contacts the introducer sheath only at each of the individual protrusions, and not at the space between the protrusions. For example, a series of surface protrusions such as second surface protrusion 122*b* may be used to protect a score line configured as a perforation.

Figure 2:
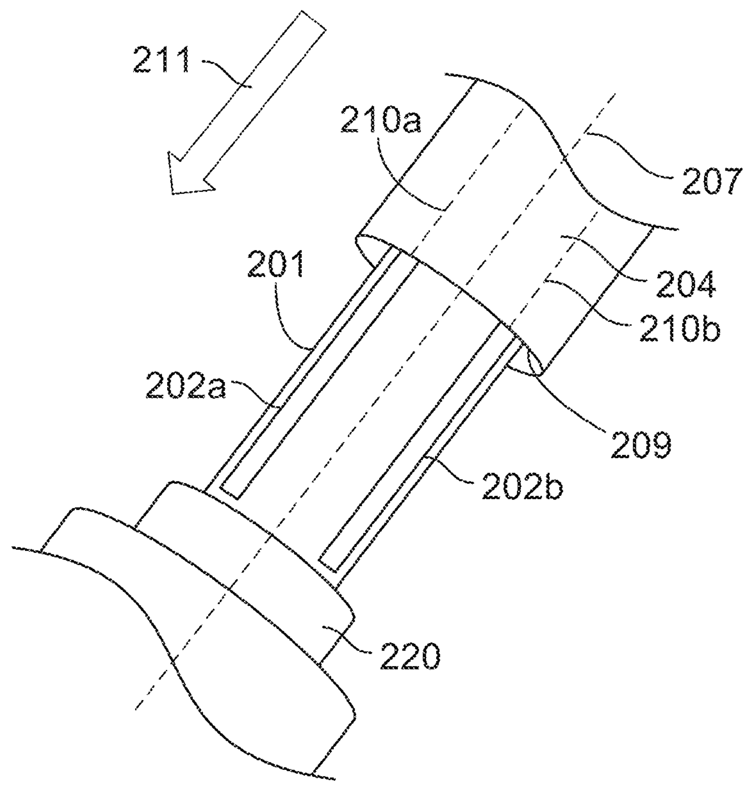
FIG. 2 shows a perspective view of a mandrel being inserted into a sheath during the manufacture process according to an embodiment.

FIG. 2 shows a perspective view of a mandrel 201 partially inserted into an introducer sheath 204 in preparation for overmolding of an introducer hub. The mandrel 201 includes a base 220, a first surface protrusion 202*a* and a second surface protrusion 202*b*. The first surface protrusion 202*a* and a second surface protrusion 202*b* are parallel to a longitudinal axis 207 of the mandrel 201. The introducer sheath 204 includes a proximal end 209, a first score line 210*a* and a second score line 210*b* aligned parallel to the longitudinal axis 207 of the mandrel 201 which coincides with a longitudinal axis 207 of the introducer sheath 204 which the introducer sheath 204 is placed on the mandrel 201. The first surface protrusion 202*a* and a second surface protrusion 202*b* are aligned with the first score line 210*a* and the second score line 210*b* of the introducer sheath 204 in order to protect the score lines and internal geometry of the introducer sheath 204 during overmolding of an introducer hub at the proximal end 209 of the introducer sheath 204. Introducer sheath 204 is inserted over the mandrel 201 in the direction of arrow 211 prior to the overmolding of the introducer hub.

Figure 3:
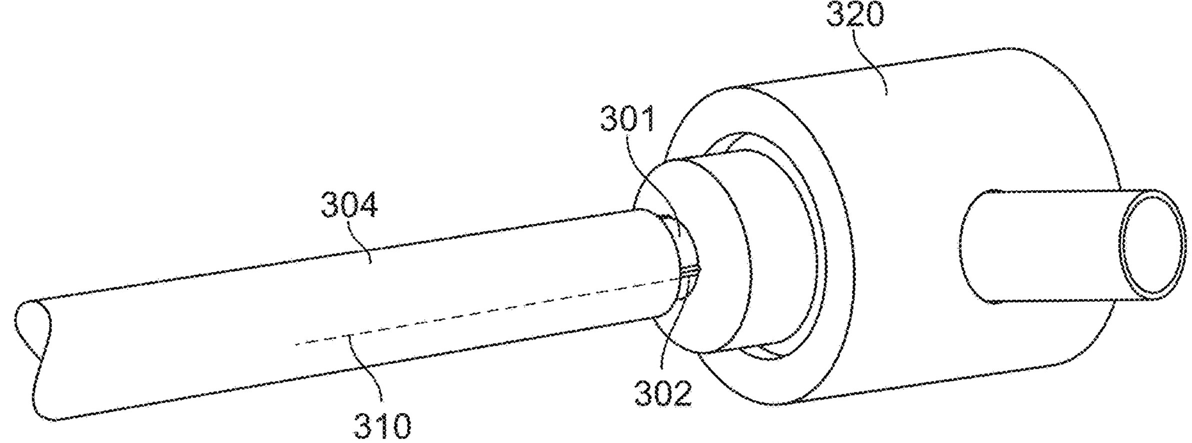
FIG. 3 shows a perspective view of a mandrel fully inserted into a sheath during the manufacture process according to an embodiment.

FIG. 3 shows a perspective view of a mandrel 301 fully inserted into an introducer sheath 304 in a final configuration prior to overmolding of an introducer hub onto the introducer sheath 304. The mandrel 301 includes a base 320 and one or more surface protrusions 302. The introducer sheath 304 includes a first score line 310 aligned parallel to a longitudinal axis 307 of the introducer sheath 304. The surface protrusion 302 is aligned with the first score line 310 to protect the first score line 310 from reflow during further processing. The introducer sheath 304 is designed to tear along the first score line 310 when the introducer hub assembly is broken. However, the first score line 310 may become damaged or be removed by the heat from the overmolding of the introducer hub body if the first score line 310 and any other score lines are not protected and maintained. The surface protrusion 302 of the mandrel 301 protects the internal geometry of the introducer sheath 304 including the first score line 310 during the overmolding of the introducer hub body so that the first score line 310 remains. The mandrel 301 is sized to fit inside the introducer sheath 304 and the surface protrusion 302 on the mandrel is likewise sized to align with and correspond to the first score line 310 on the introducer sheath 304.

Figure 4:
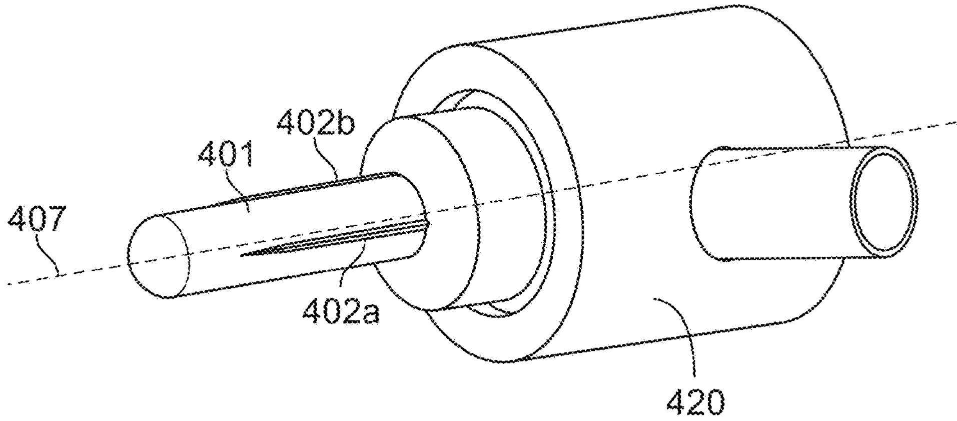
FIG. 4 shows a perspective view of a mandrel having a surface protrusion according to an embodiment.

FIG. 4 shows a perspective view of a mandrel 401 having surface protrusions 402*a* and 402*b*. The mandrel 401 includes a base 420, a first surface protrusion 402*a*, and a second surface protrusion 402*b*. The first surface protrusion 402*a* and the second surface protrusion 402*b* extend along the cylindrical mandrel 401 parallel to the longitudinal axis. The first surface protrusion 402*a* and the second surface protrusion 402*b* are sized and positioned to correspond to the internal geometry and score lines of the introducer sheath so that the internal geometry and space of the introducer sheath is maintained during the manufacture of the introducer hub on the introducer sheath.

Although two surface protrusions 402, the first surface protrusion 402*a* and the second surface protrusion 402*b*, are shown in FIG. 4, the mandrel 401 can have any suitable number or orientation of surface protrusions to protect and maintain score lines on an introducer sheath placed over the mandrel 401. The mandrel 401 may have one, two, three, four, six, eight, or any suitable number of surface protrusions. In some implementations, the mandrel 401 includes the same number of surface protrusions as the number of score lines on the introducer sheath. In some implementations, the mandrel 401 includes a smaller number of surface protrusions than the number of score lines on the introducer sheath. In such cases, the additional score lines on the introducer sheath will be removed by reflow of the plastic of the sheath during the overmolding process. Removal of unnecessary score lines during overmolding by not protecting the score lines with the mandrel may allow multiple styles of introducer hub assemblies to be prepared using a single type of introducer sheath. The surface protrusions may be aligned along the longitudinal axis 407 as shown here, or they may be oriented at an angle to the longitudinal axis or in a spiral orientation around the outer surface of the mandrel.

The first surface protrusion 402*a* and the second surface protrusion 402*b* shown in FIG. 4 are depicted as continuous raised sections of the mandrel 401. In some implementations, the surface protrusions on the mandrel 401 are configured as a series of raised dots in order to protect the specific geometry of the interior of the introducer sheath. In some implementations, the surface protrusions may be a continuous raised section configured as a ridge with an angled top, a squared top or a rounded top. The shape of the surface protrusions may be matched to a shape of the score lines in the introducer sheath.

Figure 5:
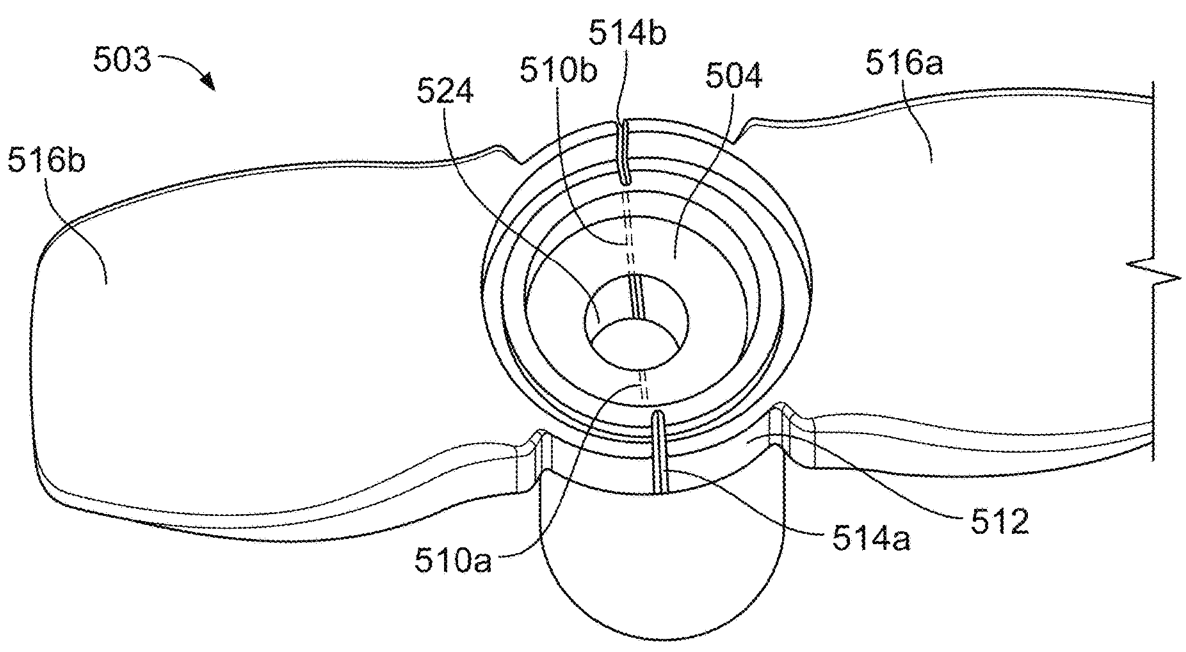
FIG. 5 shows a perspective view of a peel-away introducer hub assembly according to an embodiment.

FIG. 5 shows a perspective view of a peel-away introducer hub assembly 503. The peel-away introducer hub assembly 503 includes a hub body 512, a first wing 516*a*, a second wing 516*b*, a first notch 514*a*, a second notch 514*b*, an introducer sheath 504, a first score line 510*a*, a second score line 510*b*, and a throughgoing cavity 524. The first notch 514*a* is aligned with the first score line 510*a*, and the second notch 514*b* is aligned with the second score line 510*b*. The first wing 516*a* and the second wing 516*b* extend on opposite sides of the hub body 512, such that the first notch 514*a* and the second notch 514*b* are positioned between the first wing 516*a* and the second wing 516*b*.

A medical device or catheter may be inserted into a patient through the throughgoing cavity 524 in the introducer hub assembly 503. After the device or catheter has been inserted, an operator can break the introducer hub assembly 503 by applying a force to the first wing 516*a* and the second wing 516*b*, breaking the introducer hub assembly 503 into two or more pieces. The introducer hub assembly 503 is designed to break at the first notch 514*a* and the second notch 514*b* upon the application of this force on the first wing 516*a* and the second wing 516*b*. The alignment of the first notch 514*a* and the second notch 514*b* with the first score line 510*a* and the second score line 510*b*, respectively, allows the break force applied by the operator to break the hub body 512 to propagate from the first notch 514*a* to the first score line 510*a* and from the second notch 514*b* to the second score line 510*b* to allow the introducer hub assembly 503 to be broken into two pieces and the introducer sheath 504 to be peeled away. Good alignment of the notches with the score lines that have been protected from damage during the overmolding of the hub body 512 allows the introducer hub assembly to be easily broken and peeled with a nominal breaking force applied.

Figure 6:
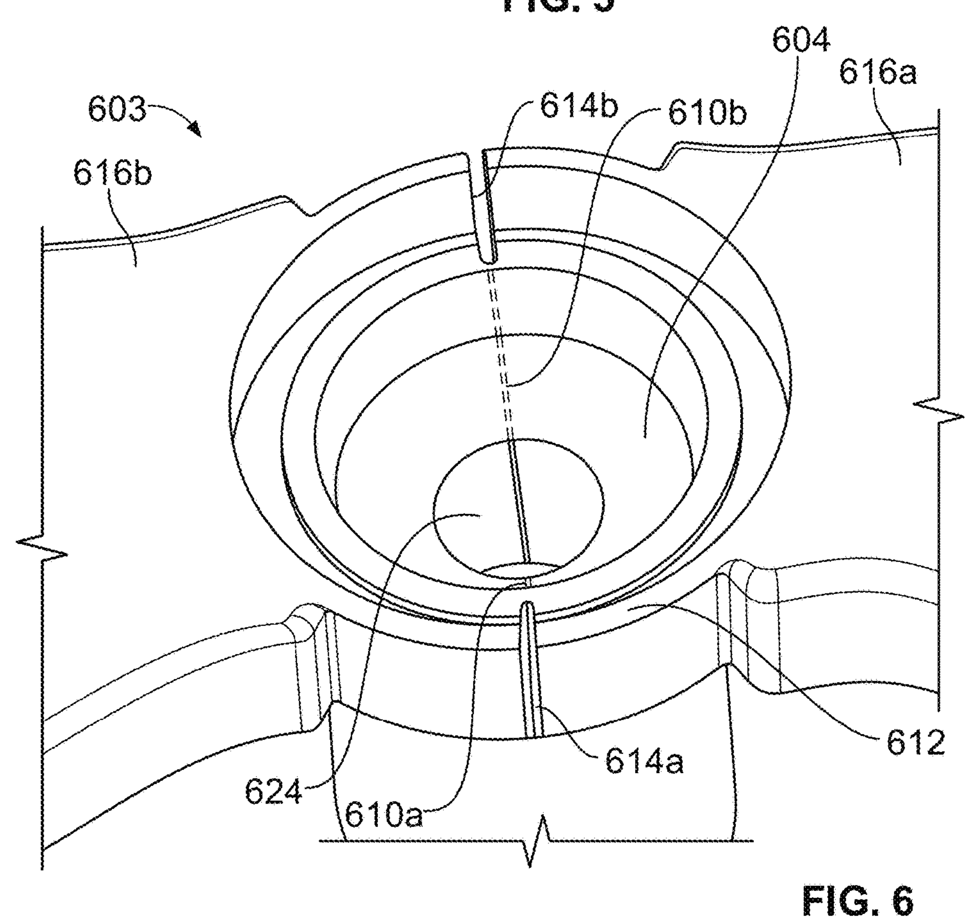
FIG. 6 shows an alternative view of a peel-away introducer hub according to an embodiment.

FIG. 6 shows an alternative view of the peel-away introducer hub 503 of FIG. 5, illustrating the alignment of the second notch 614*b* with the second score line 610*b* opposite the first notch 614*a* and first score line 610*a*. The first wing 616*a*, second wing 616*b*, and cavity 624 of FIG. 6 are the same features described above with respect to first wing 516*a*, second wing 516*b*, and cavity 524 of FIG. 5, respectively. The alignment of the second notch 614*b* with the second score line 610*b* (and first notch 614*a* and first score line 610*a*) allows the transfer of the breaking force from the hub body 612 to the introducer sheath 604. If the score line 610 of the introducer sheath 604 has not been damaged or removed by the flow of plastic material from the introducer sheath 604 during the overmolding of the introducer hub body 612, the force may be propagated from the hub body 612 to the introducer sheath 604 without incident.

If the score line 610 of the introducer sheath 604 has been damaged or removed by the reflow of plastic material from the introducer sheath 604 during overmolding, the introducer sheath 604 may not easily split apart at the hub body 612 or below the hub body 612. This may require additional or excessive force to be applied to the hub body 612 or to the introducer sheath 604 in order to break the hub body 612 and introducer sheath. Alternatively, the malfunction of the introducer hub assembly 603 due to damaged score lines in the introducer sheath 604 may result in a defective introducer hub assembly which cannot be peeled away as designed. Alternative or suboptimal methods for removal may then be used which may require additional tools.

Figure 7:
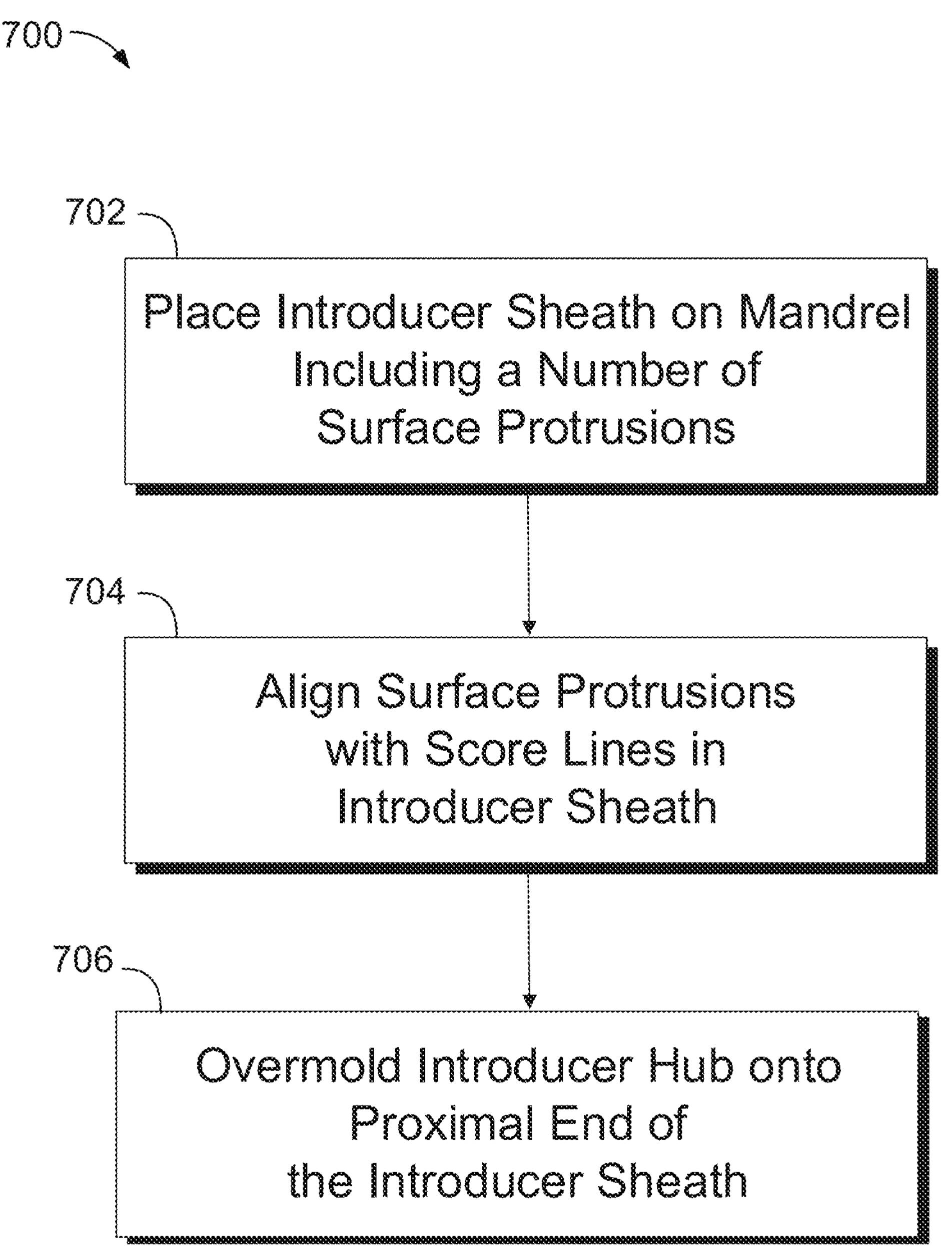
FIG. 7 shows a method for manufacturing a peel-away introducer hub according to an embodiment.

FIG. 7 shows a method 700 for manufacturing a peel-away introducer hub, such as the introducer hub assembly 103 of FIG. 1A, hub assembly 503 of FIG. 5, or any other suitable hub assembly. At step 702 the method includes placing an introducer sheath on a mandrel including a number of surface protrusions. The surface protrusions are designed to contact score lines in an interior surface of the introducer sheath in order to protect the geometry of the interior of the introducer sheath including the score lines. The mandrel may include the same number of surface protrusions as the number of score lines on the introducer sheath, or in some implementations, the mandrel includes a smaller number of surface protrusions if a number of score lines are designed to be removed during the next step. The mandrel and extruded sheath are then placed into a mold cavity allowing for molten plastic to be injected and cooled.

At step 704, the surface protrusions of the mandrel are aligned with the score lines of the introducer sheath. The introducer sheath fits tightly over the mandrel and the score lines on the interior of the introducer sheath are in contact with the surface protrusions of the mandrel. In some implementations, the surface protrusions of the mandrel may be aligned with the score lines of the introducer sheath before the mandrel is inserted into the introducer sheath, or simultaneous to insertion. The shape, size, and height of the surface protrusions may be matched to the score lines in the introducer sheath. In some implementations, the surface protrusions may be a continuous raised section configured as a ridge with an angled top, a squared top or a rounded top. The surface protrusions on the mandrel may be a variety of heights from the body of the mandrel to match the score lines in the introducer sheath. In some implementations, the surface protrusions extend from the surface of the mandrel by 0.05 mm, 0.1 mm, 0.2 mm, 0.3 mm, or any suitable height. In some implementations, there is some distance between an outer surface of the mandrel and an inner surface of the introducer sheath, but in most cases the distance is minimized such that the outer surface of the mandrel is in contact with the inner surface of the introducer sheath at least in regions which are to be protected from reflow during further manufacture. In some implementations, the distance between the outer surface of the mandrel and the inner surface of the introducer sheath in areas which are not to be protected is 0 mm, 0.1 mm, 0.2 mm, 0.3 mm, 0.4 mm or any other suitable distance. In some implementations, the surface protrusions 102*a* and 102*b* extend from the surface of the mandrel 101 by about 0.05 mm, 0.1 mm, 0.2 mm, 0.3 mm, or any suitable height. In certain implementations, the distance between the outer surface of the mandrel and an inner surface of the introducer sheath is between about 0 mm and 0.4 mm, while the protrusions extend from the outer surface of the mandrel and have a height of about 0.05 mm to 0.3 mm.

At step 706, the method includes overmolding an introducer hub onto a proximal end of the introducer sheath. The overmolding process uses heating, which may cause the plastic material of the introducer sheath to melt and reflow. The areas of the score lines which are protected by their contact with the surface protrusions of the mandrel are not covered by reflowing plastic and are maintained throughout the overmolding process. Areas which are not protected by the surface protrusions on the mandrel may reflow and fill in any additional score lines.

The overmolding of the introducer hub may also include overmolding one or more wings onto the introducer hub to aid in the breaking of the hub after use. After the introducer hub is overmolded onto the proximal end of the sheath the introducer hub and introducer sheath are removed from the mandrel. The introducer sheath includes a number of score lines which have been maintained by the mandrel during the overmolding of the introducer hub and introducer hub body. The score lines correspond to notches in the overmolded introducer hub. The introducer hub may be separated into two or more pieces at the notches and score lines after use with the application of a nominal force on the wings. Once the introducer hub has been separated at the notches and score lines, the introducer sheath may be peeled away along the score lines to remove the introducer hub assembly.

The foregoing is merely illustrative of the principles of the disclosure, and the methods and systems can be practiced other than the described implementations, which are represented for purposes of illustration and not of limitation. It is to be understood that the methods and systems disclosed herein, while shown for use in manufacture of a peel-away introducer hub and sheath, may be applied to other systems in which internal geometries of a sheath must be maintained during heat treatment.

Variations and modifications will occur to those of skill in the art after reviewing this disclosure. For example, the geometries and orientations of the surface protrusions of the mandrel can be beneficially chosen to match an internal geometry of the introducer sheath, or to complement an internal geometry or desired internal geometry. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitution, and alterations are ascertainable by one skilled in the art and could be made without departing from the scope of the information disclosed herein.

The invention claimed is:

1. A method of manufacturing a medical introducer, comprising;

placing an introducer sheath on a mandrel comprising a plurality of surface protrusions, the introducer sheath having a plurality of score lines formed on an inner surface thereof; and overmolding a plastic material onto a proximal end of the introducer sheath to form an introducer hub using a mold surrounding the proximal end of the introducer sheath, heating the plastic material wherein the plastic material is heated to such a temperature that the plastic material reflows, and reflowing the plastic material, wherein, when the introducer sheath is positioned on the mandrel, a number of the plurality of surface protrusions in contact with the plurality of score lines is less than a total number of score lines on the introducer sheath and the score lines of the plurality of score lines that are not in contact with the surface protrusions are removed by the reflowing of plastic material.

2. The method of claim 1, wherein the number of the plurality of surface protrusions on the mandrel is less than the number of the plurality of score lines formed on the introducer sheath.

3. The method of claim 2, wherein the introducer hub includes a number of notches.

4. The method of claim 3, wherein the number of notches is equal to the number of the plurality of score lines formed on the introducer sheath.

5. The method of claim 4, wherein at least one notch of the number of notches is aligned with one score line of the plurality of score lines formed on the introducer sheath.

6. The method of claim 5, wherein the introducer hub includes at least a first notch and a second notch, the first notch being aligned with a first score line of the plurality of score lines formed on the introducer sheath, and the second notch being aligned with a second score line of the plurality of score lines formed on the introducer sheath.

7. The method of claim 6, wherein the introducer hub and the introducer sheath are both configured to be broken into at least two pieces along the first and second notches and the first and second score lines.

8. The method of claim 1, wherein the number of the plurality of surface protrusions is greater than the number of score lines on the introducer sheath.

9. The method of claim 2, wherein the surface protrusions are aligned along a longitudinal axis.

10. The method of claim 2, wherein the surface protrusions are oriented at an angle to a longitudinal axis.

11. The method of claim 2, wherein the surface protrusions are aligned in a spiral orientation around the mandrel.

* * * * *